US006770033B1

(12) United States Patent
Fink et al.

(10) Patent No.: US 6,770,033 B1
(45) Date of Patent: Aug. 3, 2004

(54) IMAGING METHOD AND DEVICE USING SHEARING WAVES

(75) Inventors: Mathias Fink, Meudon (FR); Laurent Sandrin, Paris (FR); Michaël Tanter, Paris (FR); Stefan Catheline, Bais (FR)

(73) Assignee: Societe d'Elastographie Impulsionnelle pour les Systemes de Mesure de l'Elasticite (SEISME), Paris (FR)

( * ) Notice: Subject to any disclaimer, the term of this patent is extended or adjusted under 35 U.S.C. 154(b) by 0 days.

(21) Appl. No.: 09/936,462

(22) PCT Filed: Mar. 13, 2000

(86) PCT No.: PCT/FR00/00599

§ 371 (c)(1),
(2), (4) Date: Jan. 8, 2002

(87) PCT Pub. No.: WO00/55616

PCT Pub. Date: Sep. 21, 2000

(30) Foreign Application Priority Data

Mar. 15, 1999 (FR) .............................. 99 03157

(51) Int. Cl.$^7$ ............................ A61B 8/00; A61B 5/103
(52) U.S. Cl. ........................................ 600/443; 600/587
(58) Field of Search ................................ 600/438, 443, 600/447, 73, 597, 602, 625–626

(56) References Cited

U.S. PATENT DOCUMENTS

| | | | |
|---|---|---|---|
| 5,086,775 A | 2/1992 | Parker et al. | 128/660.01 |
| 5,099,848 A | 3/1992 | Parker et al. | 128/661.07 |
| 5,524,636 A | 6/1996 | Sarvazyan et al. | 128/774 |
| 5,606,971 A | 3/1997 | Sarvazyan | 128/660.02 |
| 5,810,731 A | 9/1998 | Sarvazyan et al. | 600/438 |
| 5,839,441 A | 11/1998 | Steinberg | 128/660.04 |
| 6,270,459 B1 * | 8/2001 | Konofagou et al. | 600/449 |
| 6,371,912 B1 * | 4/2002 | Nightingale et al. | 600/437 |

FOREIGN PATENT DOCUMENTS

FR 2 655 835 6/1991

OTHER PUBLICATIONS

PHD Thesis of Stefan Catheline presented to PHD jury on Nov. 10, 1998, entitled "Iterferometrie–Speckle Ultrasonore: Application a la Mesure d'Elasticite". (Ultrasonic Speckle Interferometry: Application to Elasticity Measurement).

Int'l. Search Report, PCT/FR00/00599, dated Jul. 5, 2000. Preliminary Search Report dated Mar. 1, 2000, Appl. No. FR 9903157.

O'Donnell et al., "Internal Displacement and Strain Imaging using Ultrasonic Speckle Tracking,." *IEEE*, vol. 41, No. 3, pp. 314–325 (May 1994).

Krouskop et al., "A Pulsed Doppler Ultrasonic System for Making Noninvasive Measurements of the Mechanical Properties of Soft Tissue," *J. of Rehab. Res. and Develop.* vol. 24, No. 2, pp. 1–8 (Spring 1987).

Starritt et al., "An Experimental Investigation of Streaming in Pulsed Diagnostic Ultrasound Beams," *Ultrasound in Med. & Biol.*, vol. 15, No. 4, pp. 363–373 (1989).

(List continued on next page.)

*Primary Examiner*—Francis J. Jaworski
(74) *Attorney, Agent, or Firm*—McCracken & Frank LLP

(57) ABSTRACT

The invention concerns an image method for observing the propagation of low-frequency shearing pulse wave simultaneously in multiple points of a diffusing viscoelastic medium. The method consists in transmitting at a very high rate ultrasonic compression waves enabling to obtain a succession of images of the medium; then in delayed processing of the resulting images by intercorrelation to determine in each point of each image the movements of the medium while the shearing wave is being propagated.

19 Claims, 1 Drawing Sheet

OTHER PUBLICATIONS

Lerner et al., "'Sonoelasticity' Images Derived from Ultrasound Signals in Mechanically Vibrated Tissues" *Ultrasound in Med. & Biol.*, vol. 16, No. 3, pp. 231–239 (1990).

Rudenko et al., "Acoustic Radiation Force and Streaming Induced by Focused Nonlinear Ultrasound in a Dissipative Medium," *J. Acoust. Soc. Am.*, 99 (5), pp. 2791–2798 (May 1996).

Yamakoshi et al., "Ultrasonic Imaging of Internal Vibration of Soft Tissue Under Forced Vibration," *IEEE*, vol. 37, No. 2, pp. 45–53 (Mar. 1990).

Sarvazyan et al., "Biophysical Bases of Elasticity Imaging," *Acoustical Imaging*, vol. 21, pp. 223–240 (1995).

Muthupillai et al., "Magnetic Resonance Elastography by Direct Visualization of Propagating Acoustic Strain Waves," *Science*, vol. 269, pp. 1854–1857 (Sep. 29, 1995).

* cited by examiner

IMAGING METHOD AND DEVICE USING SHEARING WAVES

FIELD OF TITLE INVENTION

The present invention relates to imaging methods and devices using shear waves.

More particularly, the invention relates to a method of imaging using shear waves to observe a diffusing viscoelastic medium which contains particles reflecting ultrasonic compression waves, in which method an elastic shear wave is generated in the viscoelastic medium and the displacement of the viscoelastic medium subjected to said shear wave is observed by means of at least one ultrasonic compression wave.

BACKGROUND OF THE INVENTION

Document U.S. Pat. No. 5,810,731 describes an example of such a method, in which the shear wave is generated locally inside the observed viscoelastic medium, by means of the radiation pressure of a modulated ultrasound wave focussed on a point to be observed. An additional ultrasound wave is then dispatched to this focal point, the reflection of the wave making it possible to ascertain certain propagation parameters of the shear wave (in particular the dynamic viscosity of the medium and its shear modulus) in the vicinity of the abovementioned focal point.

This technique has the drawback of allowing the analysis of just a single point of the viscoelastic medium under study each time a shear wave is generated. If one wishes to obtain a complete image of the observed viscoelastic medium, it is necessary to repeat the operation a very large number of times, this involving a considerable idle time (for example, several minutes) to obtain this image.

This considerable idle time renders this prior art method impractical to use.

Moreover, such an idle time may impede the use of said method to obtain an image of a living tissue, which is always in motion.

OBJECT AND SUMMARY OF THE INVENTION

An aim of the present invention is in particular to alleviate these drawbacks.

To this end, according to the invention, a method of the kind in question is essentially characterized in that the shear wave is generated by applying to the viscoelastic medium an excitation having the form of a low-frequency pulse which exhibits a central frequency f of between 20 and 5000 Hz, this low-frequency pulse exhibiting a duration of between 1/2f and 20/f, in that it comprises a propagation observation step in the course of which the propagation of the shear wave is observed simultaneously at a multitude of points in the observed medium, these points forming a substantially continuous observation field extending at least along a first axis, this shear wave propagation observation step consisting in:

emitting into the observed medium a succession of at least 10 shots of ultrasonic compression waves at a rate of between 100 and 100 000 shots per second, detecting and recording in real time the echoes generated by the reflecting particles of the viscoelastic medium at each ultrasonic wave shot, these echoes corresponding (directly or indirectly) to successive images of the observed medium, and in that said method furthermore comprises a subsequent image processing step in the course of which the images thus obtained are processed at a later time at least by cross-correlation between successive images, so as to determine at each point of the observation field a motion parameter chosen between the displacement and the strain of the viscoelastic medium, in such a way as to thus obtain a succession of images showing the evolution of the motion parameter of the viscoelastic medium under the effect of the propagation of the shear wave.

By virtue of these arrangements, a film is obtained which clearly illustrates the propagation of the shear wave in the viscoelastic medium, which may make it possible for example, in medical applications, to directly tag cancerous areas in the tissues of a patient: the propagation of the shear waves in fact occurs there very differently from the neighboring areas.

This tagging is performed much more easily than through conventional observation by simple ultrasound echography, since the propagation of the shear waves is dependent on the shear modulus of the medium, itself varying greatly between an area of healthy tissues and an area of cancerous tissues: the shear modulus typically varies in a ratio of 1 to 30 between a healthy area and a cancerous area, whereas the bulk modulus, which governs the propagation of the acoustic compression waves used in ultrasound echography, varies by only the order of 5% between a healthy tissue and a cancerous tissue.

It will be noted that the film obtained illustrates the propagation of the shear wave much more clearly than the simple succession of images given by the reflecting particles of the medium, since said film makes it possible to view at each instant the areas of the observed medium which undergo motions of the same magnitude on account of the propagation of the shear wave, whereas the succession of images of the reflecting particles would make it possible to view only a haze of bright points in motion.

In preferred embodiments of the method according to the invention, recourse may furthermore possibly be had to one and/or to the other of the following arrangements:

the duration of the low-frequency pulse is between 1/2f and 2f;

the central frequency of the low-frequency pulse is between 30 and 1000 Hz;

the observed viscoelastic medium consists of a living body comprising at least one internal organ subjected to pulsatile motions, the low-frequency pulse which generates the shear wave being constituted by a pulsatile motion of said internal organ;

the observed viscoelastic medium is delimited by an outside surface and the low-frequency pulse is applied in the vicinity of this outside surface;

the low-frequency pulse is applied by a means of excitation chosen from:
  an acoustic wave generated by at least one acoustic transducer,
  and a shock generated locally by physical contact in the vicinity of the outside surface of the viscoelastic medium;

the ultrasonic compression wave shots are emitted and the echoes generated by the reflecting particles of the viscoelastic medium are detected by means of a bank of transducers which comprises at least one transducer and which is arranged in contact with the outside surface of the viscoelastic medium, the shear wave being applied to the viscoelastic medium by imposing a pulsatile displacement on said bank of transducers;

said motion parameter is the strain of the viscoelastic medium: this arrangement is particularly useful in the last case envisaged hereinabove, since it makes it possible to dispense with the displacement of the bank of transducers, which displacement would otherwise disturb the measurement of the displacement of the points of the observation field;

in the course of the observation of the propagation of the shear wave, between 100 and 10 000 ultrasonic compression wave shots are emitted at a rate of between 100 and 100 000 shots per second;

the observation field extends at least along a plane comprising on the one hand, the first axis and on the other hand, a second axis perpendicular to the first axis;

in the course of the propagation observation step, a bank of several acoustic transducers arranged at least along the second axis is used to emit the ultrasonic compression wave shots and detect the echoes generated by the reflecting particles of the viscoelastic medium, the echoes detected by each acoustic transducer being stored directly without prior processing in the course of the propagation observation step, and the image processing step comprising a preliminary substep of forming paths in the course of which an image of the viscoelastic medium corresponding to each ultrasonic compression wave shot is generated by combining at least some of the echoes received by the various transducers;

the image processing step is followed (immediately or otherwise) by a viewing step in the course of which a film consisting of the succession of processed images is viewed under slow motion, each point of each image exhibiting an optical parameter which varies according to the value of the motion parameter assigned to this point;

the optical parameter is chosen from the gray level and the chromatic level;

the image processing step is followed (immediately or otherwise) by a mapping step in the course of which, on the basis of the evolution of the motion parameter over the course of time in the observation field, at least one propagation parameter is calculated for the shear wave at at least some points of the observation field;

the shear wave propagation parameter which is calculated in the course of the mapping step is chosen from the speed of the shear waves, the shear modulus, the attenuation of the shear waves, the shear elasticity, and the shear viscosity. Moreover, a subject of the invention is also an imaging device using shear waves to observe a diffusing viscoelastic medium which contains particles reflecting ultrasonic compression waves, this device comprising means of excitation for generating an elastic shear wave in the viscoelastic medium and means of acquisition for observing, by means of at least one ultrasonic compression wave, the displacement of the viscoelastic medium subjected to said shear wave, characterized in that the means of excitation are adapted to apply to the viscoelastic medium an excitation having the form of a low-frequency pulse which exhibits a central frequency f of between 20 and 5000 Hz, this low-frequency pulse exhibiting a duration of between 1/2f and 20/f, and in that the means of acquisition are adapted to observe the propagation of the shear wave simultaneously at a multitude of points in the observed medium, these points forming a substantially continuous observation field extending at least along a first axis, said means of acquisition being adapted for:

emitting into the observed medium a succession of at least 10 shots of ultrasonic compression waves at a rate of between 100 and 100 000 shots per second, detecting and recording in real time the echoes generated by the reflecting particles of the viscoelastic medium at each ultrasonic wave shot, these echoes corresponding (directly or indirectly) to successive images of the observed medium, and in that said device furthermore comprises image processing means adapted to process at a later time the images obtained by the observation means, at least by cross-correlation between successive images, so as to determine at each point of the observation field a motion parameter chosen between the displacement and the strain of the viscoelastic medium, in such a way as to thus obtain a succession of images showing the evolution of the motion parameter of the viscoelastic medium under the effect of the propagation of the shear wave.

In preferred embodiments of the device according to the invention, recourse may moreover possibly be had to one and/or to the other of the following arrangements:

the means of observation comprise a bank of transducers which includes at least one transducer and which is adapted to be arranged in contact with an outside surface delimiting the viscoelastic medium, the means of excitation being adapted to impose a pulsatile displacement on said bank of transducers;

said motion parameter is the strain of the viscoelastic medium;

the observation field extends at least along a plane comprising on the one hand, the first axis and on the other hand, a second axis perpendicular to the first axis, the bank of transducers comprising several transducers arranged at least along the second axis, control means being provided for selectively operating the device either in the mode of imaging by shear waves, or in a standard echography mode making it possible to acquire between 10 and 100 images per second.

BRIEF DESCRIPTION OF THE DRAWINGS

Other characteristics and advantages of the invention will become apparent in the course of the following description of several of its embodiments, given by way of nonlimiting examples, in conjunction with the appended drawings.

In the drawings.

MORE DETAILED DESCRIPTION

In the various figures, the same references designate identical or similar elements.

Figure 1:
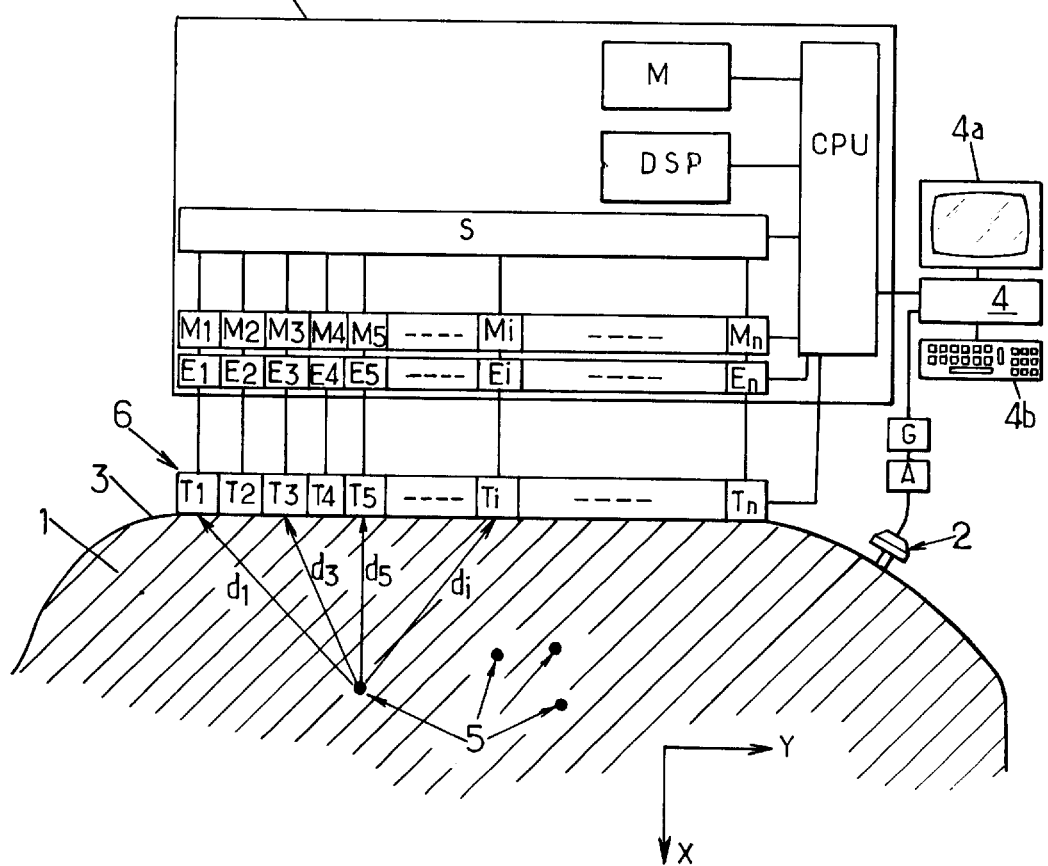
FIG. 1 is a schematic view of a device for imaging by shear waves according to one embodiment of the invention.

FIG. 1 represents an example of a device for imaging by shear waves according to the invention, for studying the propagation of elastic shear waves in a viscoelastic medium 1 which is diffusing with regard to ultrasonic compression waves, and which may for example be:

an inert body, in particular in the case of quality control for industrial applications, in particular agro-food applications, or a living body, for example a part of the body of a patient, in the case of medical applications.

This device comprises an acoustic transducer such as a loudspeaker 2 or a vibrator can which is arranged against the outside surface 3 of the observed medium 1, this surface 3 consisting for example of the skin of the patient in medical applications.

The loudspeaker 2 can be controlled by a microcomputer 4, for example by way of a low-frequency pulse generator circuit G (this circuit can consist in particular of the sound card of the microcomputer 4) and of an amplifier A, so as to apply an excitation in the form of a low-frequency pulse to the surface 3 of the observed medium, so as to generate a shear wave in the viscoelastic medium 1.

This low-frequency pulse generally exhibits an amplitude which may be of the order of 1 mm and a central frequency f of between 20 and 5000 Hz, applied for a duration of between 1/2f and 20/f. Preferably, the duration of application of the low-frequency pulse is between 1/2f and 2f and the frequency f is between 30 and 1000 Hz, this frequency typically being of the order of 50 Hz.

As a variant, the acoustic shear wave could also be obtained (with the abovementioned amplitude and frequency characteristics):

via a shock generated locally by physical contact in the vicinity of the outside surface of the viscoelastic medium, via at least one automatic mechanical actuator controlled by the microcomputer 4, via a shock applied manually by physical contact in the vicinity of the outside surface of the viscoelastic medium, or else, via a natural pulsatile motion of an internal organ of the human or animal body (for example a beating of the heart) in medical applications.

The elastic shear wave produced by the loudspeaker 2 moves with a relatively low speed Cs, of the order of a few m/s (typically, from 1 to 10 m/s in the human body), producing internal motions in the observed viscoelastic medium 1.

These motions are followed by dispatching into the medium 1, ultrasonic compression waves which interact with the diffusing particles 5 contained in the medium 1, which particles are reflecting in respect of ultrasonic compression waves. The particles 5 may be constituted by any heterogeneity of the medium 1, and in particular, when dealing with a medical application, by collagen particles present in human tissues.

To observe the propagation of the shear wave, use is therefore made of an ultrasound probe 6 arranged against the outside surface 3 of the observed medium 1. This probe dispatches, along an axis X, pulses of ultrasonic compression waves of the type of those commonly used in echography, at a frequency of for example between 1 and 100 MHz and preferably between 3 and 15 MHz. It will be noted that the probe 6 can be arranged:

either on the same side of the medium 1 as the loudspeaker 2, as represented in FIG. 1, or on the opposite side from the loudspeaker 2 with respect to the medium 1, or in any other position, for example in a transverse arrangement with respect to the loudspeaker 2.

The ultrasound probe 6 consists of a bank of n ultrasound transducers T1, T2, . . . , Ti, . . . , Tn, n being an integer number n at least equal to 1.

This probe 6 usually takes the form of a linear strip which can comprise for example n=128 transducers aligned along an axis Y perpendicular to the axis X, simultaneously dispatching their ultrasound wave pulses in such a way as to generate a "plane" wave (that is to say in this instance a wave whose wave front is straight in the X, Y plane) or any other type of wave illuminating the entire observation field.

As a variant, the bank 2 of transducers may possibly be reduced to a single transducer T1, or conversely take the form of a two-dimensional array extending for example along a plane perpendicular to the X axis.

Each of the transducers T1, T2, . . . Tn is controlled by the microcomputer 4 or by a central processing unit CPU (which is contained for example in an electronic rack 7 linked by a flexible cable to the probe 6), so as to emit successive shots of ultrasonic compression waves into the medium 2, in the course of an observation phase which may last for example less than one second and in the course of which p shots of ultrasonic compression waves are emitted (p being an integer lying between 100 and 10 000 and preferably between 1000 and 100 000), at a rate of between 100 and 100 000 shots per second and preferably between 1000 and 100 000 shots per second, in particular between 1000 and 10 000 shots per second (this rate is limited by the time for the outward/return journey of the compression wave in the medium 1, hence by the thickness of the medium 1 in the direction X: it is in fact necessary for all the echoes generated by the compression wave to have been received by the probe 6 before a new compression wave is dispatched).

The ultrasonic compression wave shots of the observation phase preferably begin just before the emission of the shear wave.

Moreover, in the case where the shear wave is generated by a pulsatile motion of an organ of a living body, it is advantageously possible to synchronize the starting of the ultrasonic compression wave shots with this pulsatile motion. For example in the case where the shear wave is generated by a heartbeat, it is possible to synchronize the starting of the ultrasonic compression wave shots with a chosen phase of the electrocardiogram.

Each of these shots gives rise to the propagation of an ultrasonic compression wave in the medium 1, with a much higher speed of propagation than the shear waves, for example of the order of 1500 m/s in the human body.

The ultrasonic wave thus generated interacts with the reflecting particles 5, thereby generating echoes or other similar disturbances of the signal, which are known per se as "speckle noise" within the field of echography.

This "speckle noise" is picked up by the transducers T1, . . . , Tn after each shot. The signal sij(t) thus picked up by each transducer Ti after shot No. j is firstly sampled at high frequency (for example from 30 to 100 MHz) and digitized in real time (for example on 8 bits, or in certain cases on 1 bit) by a sampler belonging to the rack 7 and linked to this transducer, respectively E1, E2, . . . En.

The signal sij (t) thus sampled and digitized is then stored, also in real time, in a memory Mi belonging to the rack 7 and specific to the transducer Ti.

Each memory Mi exhibits for example a capacity of the order of 1 Mb, and contains all the signals sij (t) received successively for shots j=1 to p.

At a later time, after the storage of all the signals sij(t) corresponding to one and the same shear wave propagation, the central processing unit CPU has these signals reprocessed by a summator circuit S belonging to the rack 7 (or else it performs this processing itself, or else said processing can be performed in the microcomputer 4), through a conventional process of path formation.

Signals Sj (x, y) are thus generated, each corresponding to the image of the observation field after shot No. j.

For example, a signal Sj (t) can be determined through the following formula:

$$Sj(t) = \sum_{i=1}^{n} \alpha_i(x, y) \cdot sij[t(x, y) + d_i(x, y)/V]$$

where:

sij is the raw signal sensed by transducer No. i after ultrasonic compression wave shot No. j, t(x,y) is the time taken by the ultrasonic compression wave to reach the point of the observation field with coordinates (x,y), with t=0 at the start of shot No. j, di(x,y) is the distance between the point of the observation field with coordinates (x,y) and transducer No. i, or an approximation of this distance, V is the average speed of propagation of the ultrasonic acoustic compression waves in the observed viscoelastic medium, and αi(x,y) is a weighting coefficient allowing for apodization laws (in practice, in many cases it will be possible to consider that αi(x,y)=1).

The above formula applies mutatis mutandis when the observation field is 3-dimensional (plane array of transducers), on replacing the spatial coordinates (x,y) by (x,y,z)

When the probe 6 comprises just one transducer, the path formation step is unnecessary, and we have directly Sj (x)=sj [2.x/V], with the same notation as above.

After the path formation step, should there be one, the central processing unit CPU stores in a central memory M belonging to the rack 7 the image signals Sj (x,y) or Sj(x) or Sj(x,y,z), which each correspond to shot No. j. These signals may also be stored in the microcomputer 4 when it performs the image processing itself.

These images are then processed in pairs, again at a later time, by cross-correlation. This cross-correlation can be carried out in a DSP circuit belonging to the rack 7, or be programmed into the central processing unit CPU or into the microcomputer 4.

By way of example, this cross-correlation can be done by comparing the signals Sj (x,y) and Sj+1 (x,y) (in the case of a two-dimensional observation field) over sliding spatial windows of predetermined length Δx, which may range for example from λ to 10λ, where λ is the wavelength of the ultrasonic compression waves (i.e. around 0.42 to 4.2 mm at 3.5 MHz in water or the human body). Moreover, the abovementioned windows may overlap one another over around 20% of their length along the X axis.

In the course of this cross-correlation process, a cross-correlation function <Sj(x,y), Sj+1(x,y)> is maximized so as to determine the displacement undergone by each particle 5 giving rise to an ultrasound echo, in the direction X.

Examples of such cross-correlation calculations are given in the state of the art, in particular by O'Donnell et al. ("Internal displacement and strain imaging using speckle tracking", IEEE transactions on ultrasonic, ferroelectrics, and frequency control, vol. 41, No. 3, May 1994, p. 314–325) and by Ophir et al. ("Elastography: a quantitative method for imaging the elasticity of biological tissues", Ultrasonic imag., vol. 13, p. 111–134, 1991).

A succession of displacement fields Djx(x,y) of the medium 1 under the effect of the shear wave, in the direction X, is thus obtained.

This succession of displacement fields is stored in the memory M or in the microcomputer 4 and can be viewed, in particular, by means of the screen 4a of the microcomputer, in the form of a slow-motion film where the value of the displacements is illustrated by an optical parameter such as by a gray level or by a chromatic level.

The differences in propagation of the shear wave between the areas of different characteristics of the medium 1, for example healthy tissues and cancerous tissues in the case of a medical application, are thus viewed perfectly.

This shear wave propagation film can moreover be superimposed with a conventional echography image, which may be generated by the device described above, which is able to operate:

either in the shear wave imaging mode, or in a standard echography mode, as a function of the commands received for example from the keyboard 4b of the microcomputer.

Moreover, it is also possible to calculate, rather than the displacements of each point of the observed medium 1, the strains Ejx(x,y) of the medium in the direction X, that is to say the derivatives of the displacements Djx(x,y) with respect to x.

These successive strain fields are usable as before to clearly view the propagation of the shear wave in the form of a film, and furthermore exhibit the advantage of dispensing with the displacements of the probe 6 with respect to the observed medium 1.

Figure 2:
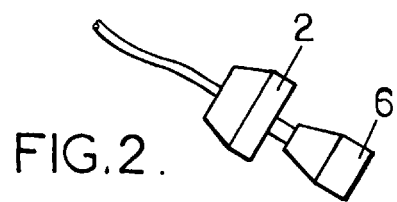
FIG. 2 is a detail view showing a variant of the device of FIG. 1.

This variant is especially beneficial in the embodiment of FIG. 2, where the probe 6 is carried by the loudspeaker or vibrator 2, this necessarily involving motions of said probe since it is the latter which itself then generates the shear wave.

On the basis of the displacement or strain fields, it is possible, if appropriate, to proceed moreover to a mapping step in the course of which, on the basis of the evolution of the motion parameter (displacement or strain) over time in the observation field X, Y (or X in the case of a single transducer, or X, Y, Z in the case of a plane array of transducers), at least one shear wave propagation parameter is calculated, either at certain points of the observation field which are chosen by the user from the microcomputer 4, or throughout the observation field.

The shear wave propagation parameter which is calculated in the course of the mapping step is chosen for example from the speed Cs of the shear waves, the shear modulus $\mu$, the attenuation α of the shear waves, the shear elasticity $\mu 1$, shear viscosity $\mu 2$.

This calculation is performed via a conventional inversion process, an example of which is given hereinbelow in the case of a two-dimensional observation field (the same process would apply mutatis mutandis in the case of an observation field having one or three dimensions, respectively for a single transducer T1 or for a plane array of transducers).

In this example, the approximation will be made that the shear viscosity $\mu 2$ is zero and that the medium is isotropic.

The wave equation giving the displacement vector D of each point of the medium 1 may be written:

$$\rho \frac{\partial^2 \overline{D}}{\partial t^2} = \Delta(\mu \cdot \overline{D}), \tag{I}$$

where ρ is the density of the medium 1, $\mu$ is the shear modulus (by assumption reduced to its real part the shear elasticity $\mu 1$ since the shear viscosity $\mu 2$ is assumed to be zero).

For the first component u of the vector D, that is to say for the displacement of the medium 1 in the direction X, we therefore have:

$$\rho \frac{\partial^2 u}{\partial t^2} = \frac{\partial^2 (\mu u)}{\partial x^2} + \frac{\partial^2 (\mu u)}{\partial y^2}. \qquad (II)$$

After temporal Fourier transform and discretization, this equation can be written in the following matrix form, which can be written for each frequency of the spectrum of the shear wave:

$$\overline{B} = \overline{H} \cdot \overline{M} \qquad (III), \text{ where:}$$

M is a vector of dimension (L+2)·(M+2)−4, each component of which equals $\mu_{lm}$, that is to say the local value of the shear modulus at each discretized point with coordinates ($x_l, y_m$), where l and m are integers lying between 0 and respectively L+1 and M+1, eliminating the pairs (l,m) equal to (0,0), (0,M+1), (L+1,0) and (L+1,M+1), L+2 and M+2 being the numbers of discretized points in the image of the medium 1 respectively along the X and Y axes, B is a vector of dimension L·M, whose components equal $-\overline{\omega}^2 \cdot \rho \cdot U_{lm}$ where $\overline{\omega}$ is the angular frequency of the low-frequency shear wave, $\rho$ is the density of the medium, $U_{lm}$ is the temporal Fourier transform of the displacement u at the point with coordinates ($x_l, y_m$), l lying between 1 and L and m lying between 1 and M, and H is a matrix of dimension L·M rows by (L+2)·(M+2)−4 columns, all of whose components are also known from the wave equation.

By juxtaposing a sufficient number of equations (III) corresponding respectively to various available items of the frequency spectrum of the shear wave, a global matrix equation is obtained which can be solved by matrix inversion, to obtain the vector M, that is to say the value of the shear modulus $\mu$ at every point of the observation field.

The local value of the speed of propagation Cs of the shear wave at each point can then be deduced therefrom, if desired, through the formula:

$$Cs = \sqrt{\frac{\mu}{\rho}}.$$

The mode of calculation would be the same if using the strains of the observed medium 1 rather than the displacements.

We claim:

1. A method of imaging using shear waves to observe a diffusing viscoelastic medium which contains particles reflecting ultrasonic compression waves, in which method an elastic shear wave is generated in the viscoelastic medium and the displacement of the viscoelastic medium subjected to said shear wave is observed by means of at least one ultrasonic compression wave, wherein the shear wave is generated by applying to the viscoelastic medium an excitation having the form of a low-frequency pulse which exhibits a central frequency f of between 20 and 5000 Hz, this low-frequency pulse exhibiting a duration of between 1/2f and 20/f, wherein said method comprises a propagation observation step in the course of which the propagation of the shear wave is observed simultaneously at a multitude of points in the observed medium, these points forming a substantially continuous observation field extending at least along a first axis, this shear wave propagation observation step consisting in:

emitting into the observed medium a succession of at least 10 shots of ultrasonic compression waves at a rate of between 100 and 100 000 shots per second, detecting and recording in real time the echoes generated by the reflecting particles of the viscoelastic medium at each ultrasonic wave shot, these echoes corresponding to successive images of the observed medium, and wherein said method furthermore comprises a subsequent image processing step in the course of which the images thus obtained are processed at a later time at least by cross-correlation between successive images, so as to determine at each point of the observation field a motion parameter chosen between the displacement and the strain of the viscoelastic medium, in such a way as to thus obtain a succession of images showing the evolution of the motion parameter of the viscoelastic medium under the effect of the propagation of the shear wave.

2. The method as claimed in claim 1, in which the duration of the low-frequency pulse is between 1/2f and 2f.

3. The method as claimed in claim 1, in which the central frequency of the low-frequency pulse is between 30 and 1000 Hz.

4. The method as claimed in claim 1, in which the observed viscoelastic medium consists of a living body comprising at least one internal organ subjected to pulsatile motions, the low-frequency pulse which generates the shear wave being constituted, by a pulsatile motion of said internal organ.

5. The method as claimed in claim 1, in which the observed viscoelastic medium is delimited by an outside surface and the low-frequency pulse is applied in the vicinity of this outside surface.

6. The method as claimed in claim 5, in which the low-frequency pulse is applied by a means of excitation chosen from:

an acoustic wave generated by at least one acoustic transducer, and a shock generated locally by physical contact in the vicinity of the outside surface of the viscoelastic medium.

7. The method as claimed in claim 5, in which the ultrasonic compression wave shots are emitted and the echoes generated by the reflecting particles of the viscoelastic medium are detected by means of a bank of transducers which comprises at least one transducer and which is arranged in contact with the outside surface of the viscoelastic medium, the shear wave being applied to the viscoelastic medium by imposing a pulsatile displacement on said bank of transducers.

8. The method as claimed in claim 7, in which said motion parameter is the strain of the viscoelastic medium.

9. The method as claimed in claim 1, in which, in the course of the observation of the propagation of the shear wave, between 100 and 10 000 ultrasonic compression wave shots are emitted at a rate of between 1000 and 100 000 shots per second.

10. The method as claimed in claim 1, in which the observation field extends at least along a plane comprising on the one hand, the first axis and on the other hand, a second axis perpendicular to the first axis.

11. The method as claimed in claim 10, in which, in the course of the propagation observation step, a bank of several acoustic transducers arranged at least along the second axis is used to emit the ultrasonic acoustic compression wave shots and detect the echoes generated by the reflecting particles of the viscoelastic medium, the echoes detected by each acoustic transducer being stored directly without prior processing in the course of the propagation observation step, and the image processing step comprising a preliminary substep of forming paths in the course of which an image of the viscoelastic medium corresponding to each ultrasonic compression wave shot is generated by combining at least some of the echoes received by the various transducers.

12. The method as claimed in claim 1, in which the image processing step is followed by a viewing step in the course of which a film consisting of the succession of processed images is viewed under slow motion, each point of each image exhibiting an optical parameter which varies according to the value of the motion parameter assigned to this point.

13. The method as claimed in claim 12, in which the optical parameter is chosen from the gray level and the chromatic level.

14. The method as claimed in claim 1, in which the image processing step is followed by a mapping step in the course of which, on the basis of the evolution of the motion parameter over the course of time in the observation field, at least one propagation parameter is calculated for the shear wave at at least some points of the observation field.

15. The method as claimed in claim 14, in which the shear wave propagation parameter which is calculated in the course of the mapping step is chosen from the speed of the shear waves, the shear modulus, the attenuation of the shear waves, the shear elasticity, and the shear viscosity.

16. An imaging device using shear waves to observe a diffusing viscoelastic medium which contains particles reflecting ultrasonic compression waves, this device comprising means of excitation for generating an elastic shear wave in the viscoelastic medium and means of acquisition for observing, by means of at least one ultrasonic compression wave, the displacement of the viscoelastic medium subjected to said shear wave, wherein the means of excitation are adapted to apply to the viscoelastic medium an excitation having the form of a low-frequency pulse which exhibits a central frequency f of between 20 and 5000 Hz, this low-frequency pulse exhibiting a duration of between $1/2f$ and $20/f$, wherein the means of acquisition are adapted to observe the propagation of the shear wave simultaneously at a multitude of points in the observed medium, these points forming a substantially continuous observation field extending at least along a first axis, said means of acquisition being adapted for:

emitting into the observed medium a succession of at least 10 shots of ultrasonic compression waves at a rate of between 100 and 100 000 shots per second, detecting and recording in real time the echoes generated by the reflecting particles of the viscoelastic medium at each ultrasonic wave shot, these echoes corresponding to successive images of the observed medium, and wherein said device furthermore comprises image processing means adapted to process at a later time the images obtained by the observation means, at least by cross-correlation between successive images, so as to determine at each point of the observation field a motion parameter chosen between the displacement and the strain of the viscoelastic medium, in such a way as to thus obtain a succession of images showing the evolution of the motion parameter of the viscoelastic medium under the effect of the propagation of the shear wave.

17. The device as claimed in claim 16, in which the means of observation comprise a bank of transducers which includes at least one transducer and which is adapted to be arranged in contact with an outside surface delimiting the viscoelastic medium, the means of excitation being adapted to impose a pulsatile displacement on said bank of transducers.

18. The device as claimed in claim 17, in which said motion parameter is the strain of the viscoelastic medium.

19. The device as claimed in claim 1, in which the observation field extends at least along a plane comprising on the one hand, the first axis and on the other hand, a second axis perpendicular to the first axis, the bank of transducers comprising several transducers arranged at least along the second axis, control means being provided for selectively operating the device either in the mode of imaging by shear waves, or in a standard echography mode making it possible to acquire between 10 and 100 images per second.

* * * * *